United States Patent [19]

Barker

[11] 4,247,538

[45] Jan. 27, 1981

[54] CONDITIONING SHAMPOO

[75] Inventor: Graham Barker, Fair Lawn, N.J.

[73] Assignee: Witco Chemical Corporation, New York, N.Y.

[21] Appl. No.: 939,543

[22] Filed: Sep. 5, 1978

[51] Int. Cl.$^3$ .............................................. A61K 7/06
[52] U.S. Cl. ................................... 424/70; 424/363; 252/117
[58] Field of Search .................................. 424/70, 363

[56] References Cited

U.S. PATENT DOCUMENTS

| | | | |
|---|---|---|---|
| 3,668,136 | 6/1972 | Barker | 252/117 |
| 3,755,559 | 8/1973 | Hewitt | 424/70 |
| 3,849,348 | 11/1974 | Hewitt | 424/70 X |
| 3,962,418 | 6/1976 | Birkofer | 424/70 |
| 3,990,991 | 11/1976 | Gerstein | 424/70 X |

OTHER PUBLICATIONS

Jellinek, "Formulation and Function of Cosmetics", Wiley–Interscience (1972), pp. 148, 147, 150.

Primary Examiner—Dale R. Ore
Attorney, Agent, or Firm—Albert L. Gazzola; Morton Friedman

[57] ABSTRACT

Aqueous compositions useful for shampooing, cleaning and conditioning hair and containing an amphoteric shampoo base, a cationic surfactant and an anionic macrocolloid polymer.

10 Claims, No Drawings

CONDITIONING SHAMPOO

BACKGROUND

The present invention is best put into perspective by the teachings of Anguillo et al., U.S. Pat. No. 3,816,616 (1974), which states in column 1 thereof, lines 20-52:

"The possibility of combining both shampoo and cream rinse action in a single composition for use in a single treatment of the hair has been investigated but until now has been considered impractical. It is well known that anionic detergents and polymers are suitable for shampooing and that cationic detergents and polymers act as cream rinses in many instances. The difficulty which investigators have encountered where these two types of materials are contacted with one another is that they either precipitate or react with one another to the extent that their individual effectiveness is significantly impaired. This is so even if they remain in solution or in a suspended state. The incompatibility of anionic and cationic compounds is well recognized by workers in the art as indicated by Sagarin in Cosmetics, Interscience Publishers, Inc., New York, 1957, where it is stated on page 538 that anionic and cationic materials are not used in combination because they react to form salts. Thus, in practice, the anionic detergent shampoo is used first, followed by a separate cream rinse with a cationic material.

"The removal of dirt and excess oils from the hair with a shampoo is conventional but it has been long recognized that after shampooing the hair is difficult to manage, being inclined to knot and tangle and be usually only difficulty (sic) combable. The problem of wet combing has been dealt with by treating shampooed hair with a cream rinse which coats the hair shafts and causes the individual filaments in a tress to resist tangling and matting because of the cream rinse residue retained by them. The commonly accepted method, prior to the present invention, has been to shampoo the hair followed by rinsing and the separate application of a cream rinse followed by a second rinse".

This patent teaches making a shampoo/cream rinse composition by combining a cationic polymer [1] with an anionic detergent, such sodium lauryl sulfate, triethanolammonium lauryl sulfate, sulfosuccinate half ester amide, [2] and the like, and finding out that the components are compatible.

[1] Polymer JR-400, a product of the Union Carbide Corporation, is an O-alkyl-trimethylammoniumchloride substituted anhydroglucose polymer.
[2] Emcol 4161, a product of the Witco Chemical Corporation.

"This compatibility is totally unexpected since, in addition to the general knowledge that anionic and cationic substances tend to combine and salt out of solution, the technical information supplied by the maker of Polymer JR specifically states that 'aqueous solutions of Polymer JR are not compatible with anionic polymers such as sodium carboxymethylcellulose and they are also incompatible with anionic detergents.'" Anguillo et al., col. 3, first full paragraph.

The long-recognized effect of combining anionic and cationic substances is a product known as a poissage, which is otherwise described as a glue-like substance or gunk.

As a consequence, shampoos have conventionally been made of foamy amphoteric compounds and cationic compounds and cationic surface active agents. A separate cream rinse is applied, if desired, following rinsing out of the shampoo composition from the hair, the cream rinse being used to condition the hair.

The Anguillo et al. finding combines—as indicated supra—"both shampoo and cream rinse action" in one composition. The cationic component thereof, viz., O-alkyltrimethylammoniumchloride substituted anhydroglucose polymer, is not a "household item", so to speak. As a result, it adds to the cost of conditioning shampoos containing same.

Subsequent to the Anguillo et al. patent of 1974, a U.S. Pat. No. 3,990,991 issued on Nov. 9, 1976 to patentee Terry Gerstein. It discusses the Anguillo et al. patent:

"Until recently the desirable properties of both a shampoo and a cream rinse could not be provided in a single formulation, and separate shampoo and cream rinse preparations had to be used if the desirable properties of each of these preparations were to be obtained. Claims have recently been made that a shampoo formulated to contain Polymer JR Resin, a water-soluble cationic cellulosic resin described in U.S. Pat. No. 3,472,840, possessed the desirable properties of both a shampoo and a cream rinse.

"However, although such preparations do clean and condition the hair, their detangling effects leave much to be desired. At best, these preparations, which contain in addition to Polymer JR Resin, triethanolamine lauryl sulfate and lauric diethanolamide, are inefficient detanglers when compared to cream rinses used independently. Furthermore, these preparations are formulated at an alkaline pH because not only do the anionic and alkanolamide surfactants function better on the alkaline pH side, but they are chemically unstable at acid pH. It is, however, preferable to use preparations of lower alkalinity for the hair." Col 1 of U.S. Patent No. 3,990,991, ls. 15–37.

Gerstein combines (a) an amphoteric surfactant, such as a substituted imidazoline [e.g., MIRANOL (trademark of Miranol Chemical Company, Inc.)], a long-chain N-alkyl derivative of beta-aminopropionic acid, and the like; (b) a cryptoanionic surfactant, such as SANDOPAN DTC (trademark of Sandoz Chemical Works, New York, NY), and (c) a cationic surfactant including, inter alia, Polymer JR, described supra, in footnote 1. According to the Gerstein patent, column 3, ls. 3–6, "[t]he amounts of amphoteric and cryptoanionic surfactants are adjusted so that the pH of the final formulation will be between about 3.0 and 8.5, preferably about 6.2 6.9."

The following additional references (patents and literature) are considered of varying interest, but nonanticipatory of the invention hereinafter claimed:

| Patentee/s | U.S. Pat. No. | Issue Date |
|---|---|---|
| Tarasov et al. | 3,996,146 | December 7, 1976 |
| Birkofer | 3,962,418 | June 8, 1976 |
| Wendler et al. | 3,926,840 | December 16, 1975 |
| Hewitt | 3,849,348 | November 19, 1974 |
| Corey | 3,793,210 | February 19, 1974 |
| Hewitt | 3,755,559 | August 28, 1973 |
| Olson, Jr., et al. | 3,697,452 | October 10, 1972 |
| Barker | 3,668,136 | June 6, 1972 |
| Hewitt | 3,642,977 | February 15, 1972 |

Also, the following scientific literature references have been uncovered:

Balsam et al., "Cosmetics Science and Technology", 2nd Ed., Vol. 2, March 1972, published by Wiley Interscience, New York, NY, p. 136;

Gerstein, T., "Cosmetics and Toiletries," Vol. 93, February 1978, pages 15–44, Allured Publishing Corp., article entitled "Trends and aspects of contemporary shampoos II Developments in shampoo technology"; and Raphael, Leon, "Manufacturing Chemist", March 1958, pages 105–108, article entitled "Nonionic Surface Active Agents I. Chemistry and Manufacture."

Reference shall now be made to several of the above references as follows:

U.S. Pat. No. 3,793,210 to Corey concerns surfactant/shampoo compositions having improved solubility and foaming characteristics and made up of a keto acid in combination with surfactants, brighteners, conditioners, and the like. Typical surfactants are the ampholytic surface active agents, such as the fatty imidazoline, including those known as MIRANOL. If desired, anionic surface active agents may be present, such as the alkyl sulfates.

U.S. Pat. No. 3,697,452 to Olson, Jr. et al., discloses a conditioning shampoo containing an amphoteric detergent, e.g., MIRANOL, a higher alkyl amine oxide and a quaternary ammonium salt (cationic surfactant).

U.S. Pat. No. 3,755,559 to Hewitt is directed to shampoo compositions containing (i) a higher alkyl betaine, (ii) a higher alkyl amine oxide, (iii) a saturated fatty acid salt, and (iv) water. Optional components, pursuant to the patentee, include, e.g., a thickener, such as a methyl cellulose.

U.S. Pat. No. 3,642,977 to Hewitt prepares a shampoo from an amphoteric imidazoline, an amide-substituted carboxylic acid, and water.

U.S. Pat. No. 3,849,348 to Hewitt uses an alkyl betaine (e.g., cocoa betaine), a tertiary amine oxide, a quaternary nitrogen compound, and water to fashion his detergent composition suitable for use as a shampoo, skin cleansing liquid, and/or fabric-washing or conditioning composition. Adjuvant materials, such as gum, alkaline or acid buffers, may be present in this Hewitt composition.

Balsam et al., alluded to above, is directed to a hairdressing containing gum arabic, gelatin, and the like, in the concentration of 0.5 to about 2 percent.

As will be evident, infra, these references fail, singly or in combination, to anticipate or suggest the present discovery. This will be better understood from the description of the invention which is hereinafter provided.

INVENTION

The present invention relates to novel compositions useful for shampooing, cleaning and conditioning hair. More particularly, the instant discovery concerns aqueous conditioning shampoos which not only clean and shampoo but, upon rinsing, deposit a polymeric component on the hair which imparts very desirable properties to the hair, such as body and curl retention. The polymeric component is an anionic macrocolloid polymer, viz., gum arabic.

Still more particularly, the conditioning shampoo of the present invention comprises a clear solution of (i) a foamy amphoteric shampoo base, (ii) a cationic surfactant, (iii) gum arabic, and (iv) water. On a percentage basis, by weight, component (i) is present in the concentration of about 5.0 to about 20.0 percent, preferably about 8.0 to about 12.0, component (ii) is present in the concentration of about 1.0 to about 15.0 percent, preferably about 2.0 to about 8.0, component (iii) is present in the concentration of about 0.20 to about 5.0 percent, preferably about 1.0 to about 3.0, and component (iv) is the balance. The percentages are based upon the total weight of the aqueous conditioning shampoo solution as prepared.

It is believed that the anionic macrocolloid polymer is made substantive to the hair, when in the presence of the cationic surfactant and upon rinsing after shampooing, through a coacervation mechanism, known as "complex coacervation". Complex coacervation includes a process wherein at least two oppositely electrically charged hydrophilic polymeric materials complex with one another whereby their solubility in water is decreased. An emergent phase contains substantially all of both hydrophilic colloidal materials utilized in forming the complex.

It is within the purview of the art and the present invention to include conventional additives in conventional minor quantities. For example, thickeners, fragrants, preservatives, and the like, may be added to contribute to the elegance of the clear conditioning shampoo composition.

Typical compositions contemplated herein and having the aforementioned properties are the following:

TABLE 1

| (i) Amphoteric Component | (ii) Cationic Component | (iii) Anionic Component |
|---|---|---|
| cocoa betaine 10% | polypropoxylated (9)[3] quaternary ammonium chloride 4% | gum arabic 4% |
| cocoa betaine 12% | polypropoxylated (9)[4] quaternary ammonium chloride 8% | gum arabic 2% |
| lauryl betaine 7% | polypropoxylated (25)[5] quaternary ammonium chloride 13% | gum arabic 0.6% |

[3] Polyoxypropylene (9) methyl diethyl ammonium chloride
[4] Polyoxypropylene (9) methyl diethyl ammonium chloride
[5] Polyoxypropylene (25) methyl diethyl ammonium chloride The foamy amphoteric shampoo base detergents herein contemplated are well known. Those herein disclosed are illustrative.

Suitable are the sultaine and betaine types having the following general formula:

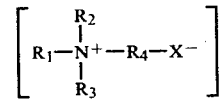

wherein $R_1$ is an alkyl group having from about 8 to about 18 carbon atoms, $R_2$ and $R_3$ each represent a lower alkyl having 1 to 3 carbon atoms, $R_4$ is an alkylene or a hydroxy-substituted alkylene group having from about 1 to about 3 carbon atoms, and X is an anion selected from $SO_3^-$ (sultaine) and $COO^-$ (betaine).

Preferred amphoteric detergents are cocoa betaine and lauryl betaine, i.e.:

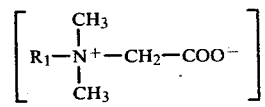

Other suitable amphoteric shampoo base detergents include: the alkyl beta-aminopropionates, $R_1N(H)C_2H_4COOM$; the alkyl beta-iminodipropionates, $R_1N(C_2H_4COOM)_2$; and the long chain imidazole derivatives, sold under the trade name "Miranol" by the Miranol Chemical Company, Inc., having the following general formula:

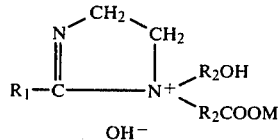

In the last 3 formulae $R_1$ is alkyl having about 12 to about 18 carbon atoms, $R_2$ is an alkylene or hydroxyalkylene group having 1 to 4 carbon atoms, and M is a water-soluble cation, e.g. an alkali metal, ammonium or alkylolammonium.

The higher alkyl moieties of the foregoing aminopropionates and iminopropionates may be, for example, derived from cocoa fatty alcohol, lauryl alcohol, myristyl alcohol, cetyl alcohol, stearyl alcohol, or blends of such alcohols; whereas, the higher alkyl moieties of the imidazole derivatives is derived from a higher fatty acid, e.g., the fatty acid mixture obtained from coconut oil or tallow. Suitable detergents include sodium N-lauryl beta-aminopropionate, di-sodium N-lauryl beta-aminopropionate, and the sodium salt of 2-laurylcycloimidium-1-hydroxy, 1-hydroxyethanoic acid, 1-ethanoic acid.

The cationic surfactants of the present invention are commonly known as "polypropoxylated quaternary ammonium chlorides." They are so called herein to mean compounds corresponding to the following formula:

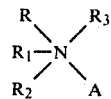

wherein
R is alkyl $C_1$–$C_3$;
$R_1$ is selected from (a) $C_1$–$C_3$, and (b)

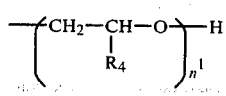

wherein $R_4$ is alkyl $C_1$–$C_4$; and compounds wherein R and $R_1$ are joined together to form, with the N atom of formula (I), supra, a member of the group consisting of piperidine, methyl piperidine, and pyrrolidine;

$R_2$ is

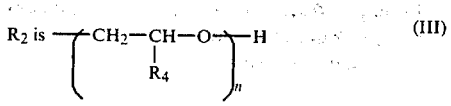

in which $R_4$ is alkyl $C_1$–$C_4$, and the total number of carbon atoms in $R_2$ is at least 18;

$R_3$ is a member of the group consisting of alkyl $C_1$–$C_4$, alkenyl $C_1$–$C_4$, benzene, methyl benzenes, ethyl benzenes,

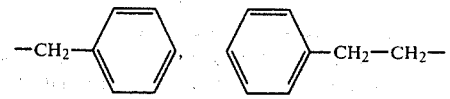

and their methyl and ethyl nuclearly substituted derivatives, and the mono-halo mono-nitro nuclearly substituted derivatives of the foregoing;

A is an anion; and n and $n^1$ are numbers the of sum which does not exceed 60.

Preferred polypropoxylated quaternary ammonium chlorides are those of formula (I) wherein R and $R_1$ are alkyl $C_1$–$C_3$; $R_3$ is alkyl $C_1$–$C_4$; $R_2$ is the polyoxypropylene of formula (III), above, wherein n is a number from 9 to 30; and the anion of formula I, denoted as A, is chlorine. Typical of these are polyoxypropylene (9) methyl diethyl ammonium chloride, polyoxypropylene (25) methyl diethyl ammonium chloride, and the like.

It has been found that best results are achieved with the conditioning shampoo of the present invention when it has a pH of about 4.5 to about 7.5, preferably about 5.0 to about 7.0.

EXAMPLES

The present invention will better be understood from the following examples which are intended to be illustrative and not unduly limitative:

EXAMPLES: AA1, AA1a, AA2 and AA3

A shampoo base is prepared by (i) blending, in an aqueous medium, a foaming amphoteric, viz., lauryl betaine (45% concentration in $H_2O$) with a polypropoxylated quaternary ammonium chloride cationic surfactant, viz., polyoxypropylene (9) methyl diethyl ammonium chloride, and Emcol 5170 (lauryl diethanolamide, a thickener), and (ii) adding to the resulting solution mixture a pre-determined amount of gum arabic.

The pH of the solution depends on the relative concentrations of the components present in the aqueous medium. It is preferably maintained to within the range hereinbefore given. TABLE II, infra, shows the concentrations, pH, and appearance of the aqueous shampoo as prepared (i.e., in concentrated form); and this same table records the foaming characteristics, curl retention properties [at 65% relative humidity (RH)] and appearance of the conditioning shampoo on dilution with $H_2O$. Appearance is reported as clear (CR) or cloudy (CY). Cloudiness is brought about, it is believed, by the coacervation mechanism hereinabove described. The solids suspended in the cloudy (dilute) aqueous solution are deposited on the hair when rinsing the shampoo, thus providing the very desirable conditioning characteristics described supra (e.g., body, curl retention, and the like) without the need for applying separate conventional conditioners following rinsing after shampooing.

Testing for curl retention is carried out by first applying a two-gram sample of each shampoo to prepared hair tresses in the following manner: each hair tress is first rinsed in running tap water at a typical wash temperature until thoroughly wetted. A shampoo sample is then applied directly to the hair by pouring it on the hand-held tress. The shampoo is worked into the hair by washing between the hands for about one minute, thereby producing a lather. Next, the shampoo is removed by means of a running water rinse for one minute, and then the hair is untangled by combing, if necessary. The tress is washed again with the shampoo for two minutes and given a final one minute running water rinse. The tress is then subjected to a curl retention test.

In this latter test, the tress, while still wet from the final shampoo rinse as aforedescribed, is wound and held in place on a curler. The tress is then hung to dry at room temperature. After drying, the hair tress is removed from the curler, allowed to hang free, and the length of curl measured.

The tress is then placed in a humid environment and the length of hair measured with respect to time. This humid environment is provided by a desiccator containing, at room temperature, saturated ammonium sulfate, which provides approximately 80% relative humidity (RH), or, alternatively, saturated sodium nitrite, which provides approximately 65% relative humidity (RH). Measurements are taken at one-half hour intervals over a four-hour span for determining the length of curl retained, expressed as a percentage of the original length. Qualities such as hair manageability (i.e. ease of combing), and so-called "flyaway" can also be observed with the tress treated in this manner.

The pH of the shampoo (concentrate) is taken in a conventional manner. Foaming is determined by adding four drops of shampoo to 20 ml of distilled water. This solution is shaken 20 times in a 100 ml stoppered graduate and the foam height measured.

In the following TABLE II, concentrations are recited in parts by weight (based upon the total weight of the concentrate formulated), which parts by weight convert, for each component, to percentages by weight within the broad ranges hereinabove specified. Note that the amphoteric component is only at 45% strength. In TABLE II, where no percentages appear alongside the component, the component is neat.

TABLE II

| Component | AA1 | AA1a | AA2 | AA3 |
|---|---|---|---|---|
| Lauryl betaine (45%) | 36 | 36 | 36 | 36 |
| Polypropoxylated (9) methyl ethyl Quaternary | | | | |
| Ammonium Chloride | 6 | 6 | 6 | 6 |
| Alkanolamide[a] | 4 | 4 | 4 | 4 |
| Gum Arabic | 3 | 3 | 1.5 | 3 |
| Water | 151 | 151 | 151 | 151 |
| pH | 6.5 | 6.5 | 6.5 | 5.1 |
| Appearance (concentrated) | CR | CR | CR | CR |
| Foam Height (mm) | 40 | 40 | 40 | 40 |
| Appearance (dilute) | CY | CY | CY | CY |
| Curl Retention (at 65% RH) | — | 93 | 93 | 85 |

[a]Emcol 5170, Witco Chemical Corporation. "Emcol" is a registered trademark of Witco Chemical Corporation, New York, N.Y., for lauryl diethanolamide or myristyl diethanolamide, and mixtures of these.

EXAMPLES: AA4–AA12

In TABLE III, infra, the procedures followed for preparing and testing the examples given in TABLE II, supra, are followed. Note, however, that instead of parts by weight being recited in TABLE III, percentages by weight are given. The amount of water present (but not recited) in each shampoo concentrate is the quantum sufficit, by weight, to make 100%. Of course, pH is adjusted, as desired, to a figure in the range hereinabove recited.

TABLE III

| Component | AA4 | AA5 | AA6 | AA7 | AA8 | AA9 | AA10 | AA11 | AA12 |
|---|---|---|---|---|---|---|---|---|---|
| Cocoa betaine (50%) | 7 | — | — | — | 10 | — | — | 19 | — |
| Alkyl ($C_{16}$) beta aminopropionate (ammonium cation) | — | 10 | — | — | — | — | 8 | — | 9 |
| Alkyl ($C_{15}$) beta iminodipropionate (sodium cation) | — | — | 14 | — | — | 12 | — | — | — |
| $H_{29}C_{14}-\underset{OH^-}{\overset{N-CH_2}{\underset{\|}{C}}}-\underset{CH_2COONa}{\overset{CH_2CH_2OH}{\underset{\|}{N}}}$ | — | — | — | 16 | — | — | — | — | — |
| Polypropoxylated quaternary[6] ammonium chloride | 6.0 | 4.0 | 6.0 | 4.5 | 5.2 | 5.8 | 4.2 | 5.0 | 5.2 |
| Gum Arabic | .9 | 4.0 | 2.0 | 1.7 | 3.0 | 2.4 | 2.8 | 1.7 | 1.8 |
| pH | 5.3 | 6.1 | 7.2 | 5.9 | 6.7 | 6.8 | 6.8 | 7.0 | 7.0 |
| [6]Polyoxypropylene methyl diethyl ammonium chloride in which the no. of oxypropylene moieties is | (9) | (25) | (19) | (9) | (25) | (9) | (19) | (9) | (9) |

EXAMPLE: AA13

Example AA8 is repeated in every essential respect, with the exception that the amphoteric component is the following sultaine:

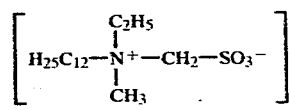

The pH is adjusted to 6.9.

EXAMPLE: AA14

Example AA13 is repeated in every essential respect, with the exception that the cationic surfactant is as in formula I, supra, wherein: R is $C_2$; $R_1$ is a moiety from formula II, supra, in which $R_4$ is $C_1$ and $n_1$ is 3; $R_2$ is a moiety from formula III, above, in which $R_4$ is $C_2$ and n is 9; $R_3$ is $C_3$; and A is Cl. The pH is adjusted 7.0.

EXAMPLE: AA15

Example AA2 is repeated in every essential respect, with the exception that the cationic surfactant is taken from formula I, supra, wherein R and $R_1$ are joined together to form, with N, methyl piperidine; $R_2$ is a moiety from formula III, above, wherein $R_4$ is $C_1$ and n is 9; $R_3$ is benzene; and A is Cl. The pH is adjusted to 4.9.

Pursuant to statutory requirements, there are described above the invention and what are now considered its best embodiments. It should be understood, however, that the invention can be practiced otherwise than as specifically described, within the scope of the appended claims.

What is claimed is:

1. An aqueous conditioning shampoo composition which comprises, percentages given being by weight based upon the total weight of the composition:
   (i) from about 5.0 to about 20.0 percent of a foamy amphoteric shampoo base detergent selected from the group consisting of (1) sultaine and betaine compounds having the following general structural formula:

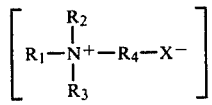

wherein $R_1$ is an alkyl group having from about 8 to about 18 carbon atoms, $R_2$ and $R_3$ each represent a lower alkyl having 1 to 3 carbon atoms, $R_4$ represents alkylene and hydroxy-substituted alkylene group having from about 1 to about 3 carbon atoms, and X is an anion selected from $SO_3^-$, sultaine, and $COO^-$, betaine; (2) alkyl beta-aminopropionate, $R_1N(H)C_2H_4COOM$; (3) alkyl beta-iminopropionate, $R_1N(C_2H_4COOM)_2$; and (4) long chain imidazole derivatives having the following structural formula:

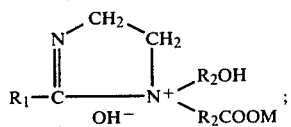

in the last 3 formulae, supra, $R_1$ is alkyl having about 12 to about 18 carbon atoms, $R_2$ is an alkylene or hydroxyalkylene group having 1 to 4 carbon atoms, and M is a water-soluble cation;
   (ii) from about 1.0 to about 15.0 percent of a polypropoxylated quaternary ammonium chloride cationic surfactant having the following structural formula:

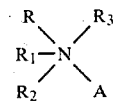

wherein R is alkyl $C_1$–$C_3$; $R_1$ is selected from

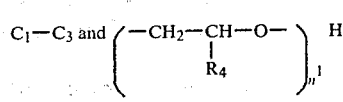

wherein $R_4$ is alkyl $C_1$14 $C_4$; and compounds wherein R and $R_1$ are joined together to form, with the N atom of formula (I), supra, a member of the group consisting of piperidine, methyl piperidine, and pyrrolidine;

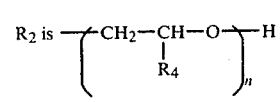

in which $R_4$ is alkyl $C_1$14 $C_4$, and the total number of carbon atoms in $R_2$ is at least 18; $R_3$ is a member of the group consisting of alkyl $C_1$-$C_4$, alkenyl $C_1$14 $C_4$, benzene, methyl benzene,

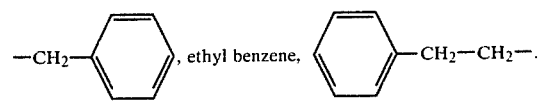

and their methyl and ethyl nuclearly-substituted derivatives, and the mono-halo mono-nitro nuclearly-substituted derivatives of the foregoing; A is an anion; and n and $n^1$ are numbers of the sum of which does not exceed 60;
   (iii) from about 0.20 to about 5.0 percent gum arabic; and
   (iv) the balance water.

2. The composition of claim 1 wherein component (i) is present in the concentration range of about 8.0 to about 12.0 percent; component (ii) is present in the concentration range of about 2.0 to about 8.0 percent; and component (iii) is present in the concentration range of about 1.0 to about 3.0 percent.

3. The composition of claim 1 in which component (i) is lauryl betaine.

4. The composition of claim 2 in which component (i) is lauryl betaine.

5. The composition of either claim 1 or claim 2 in which component (ii) is a polypropoxylated quaternary ammonium chloride of the formula

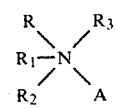

wherein R and $R_1$ each represent alkyl $C_1$–$C_3$; $R_3$ is alkyl $C_1$–$C_4$; $R_2$ is

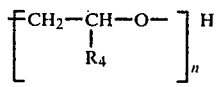

in which n is an integer from 9–30; $R_4$ is $C_1$–$C_4$; and A in the former formula is Cl.

6. The composition of claim 3 in which component (ii) is polyoxypropylene (9) methyl diethyl ammonium chloride.

7. The composition of claim 4 in which component (ii) is polyoxypropylene (9) methyl diethyl ammonium chloride.

8. The composition of either claim 4 or claim 2 wherein the pH of the composition is in the range of about 4.5 to about 7.5.

9. The composition of either claim 1 or claim 2 wherein the pH of the composition is in the range of about 5.0 to about 7.0.

10. The composition of either claim 1 or claim 2 in which component (i) has the structural formula

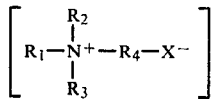

wherein $R_1$ is an alkyl group having from about 8 to about 18 carbon atoms, $R_2$ and $R_3$ each represent a lower alkyl having 1 to 3 carbon atoms, $R_4$ is an alkylene or a hydroxysubstituted alkylene group having from about 1 to about 3 carbon atoms, and X is an anion selected from $SO_3^-$, sultaine, and $COO^-$, betaine.

* * * * *